(12) United States Patent
Lee

(10) Patent No.: US 11,051,845 B2
(45) Date of Patent: Jul. 6, 2021

(54) NON-SURGICAL CHEST TUBE INTRODUCER

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 945 days.

(21) Appl. No.: 15/406,705

(22) Filed: Jan. 14, 2017

(65) Prior Publication Data
US 2018/0199959 A1    Jul. 19, 2018

(51) Int. Cl.
*A61B 17/34* (2006.01)
*A61B 17/3211* (2006.01)
*A61B 17/00* (2006.01)

(52) U.S. Cl.
CPC ...... *A61B 17/3415* (2013.01); *A61B 17/3474* (2013.01); *A61B 2017/00951* (2013.01); *A61B 2017/347* (2013.01); *A61B 2017/3419* (2013.01); *A61B 2017/3427* (2013.01); *A61B 2017/3482* (2013.01); *A61B 2017/3486* (2013.01); *A61B 2017/3492* (2013.01); *A61M 2210/101* (2013.01)

(58) Field of Classification Search
CPC combination set(s) only.
See application file for complete search history.

(56) References Cited

U.S. PATENT DOCUMENTS

| 3,394,705 A * | 7/1968 | Abramson | A61M 25/0017 604/43 |
| 3,435,826 A * | 4/1969 | Fogarty | A61B 17/22 606/194 |
| 3,771,527 A * | 11/1973 | Ruisi | A61M 1/85 604/43 |
| 4,335,723 A * | 6/1982 | Patel | A61L 29/041 604/97.02 |
| 4,429,856 A * | 2/1984 | Jackson | F16L 37/38 251/149.1 |
| 4,946,444 A | 8/1990 | Heimke et al. | |
| 4,959,054 A * | 9/1990 | Heimke | A61M 39/0247 604/175 |
| 5,242,415 A * | 9/1993 | Kantrowitz | A61M 39/0247 604/175 |
| 5,308,325 A * | 5/1994 | Quinn | A61J 15/0015 604/174 |
| 5,697,946 A * | 12/1997 | Hopper | A61B 17/3421 606/185 |
| 6,231,547 B1 * | 5/2001 | O'Hara | A61M 25/02 604/174 |
| 6,524,283 B1 * | 2/2003 | Hopper | A61B 17/3421 604/264 |
| 6,623,502 B2 * | 9/2003 | Wagner | A61B 17/3403 606/185 |
| 6,682,506 B1 * | 1/2004 | Navarro | A61M 25/02 604/174 |
| 6,860,892 B1 * | 3/2005 | Tanaka | A61B 17/00008 600/201 |
| 7,226,462 B2 * | 6/2007 | Tanaka | A61B 17/00008 600/207 |

(Continued)

*Primary Examiner* — Guy K Townsend

(57) ABSTRACT

The present invention provides a chest tube introducer which can be inserted without a need of surgical procedures. The chest tube introducer comprises a series of compartmentalized leakproof sealing devices, which is configured for safe introduction of the chest tube introducer minimizing a risk of pneumothorax.

7 Claims, 12 Drawing Sheets

(56) References Cited

U.S. PATENT DOCUMENTS

| | | | | |
|---|---|---|---|---|
| 7,264,596 B2* | 9/2007 | Burburk | ............ | A61B 10/0266 600/567 |
| 7,329,228 B2* | 2/2008 | Burbank | ............ | A61B 10/0266 600/567 |
| 7,494,460 B2* | 2/2009 | Haarstad | ................ | A61M 1/84 600/37 |
| 8,105,231 B2* | 1/2012 | Kasahara | ............ | A61B 18/1482 600/114 |
| 8,142,467 B2* | 3/2012 | Hart | ................ | A61M 25/0662 606/185 |
| 8,229,553 B2* | 7/2012 | Burbank | ................ | A61B 90/39 600/546 |
| 8,287,503 B2* | 10/2012 | Albrecht | ............ | A61B 17/3421 604/264 |
| 8,449,449 B2* | 5/2013 | Haarstad | ................ | A61M 1/84 600/37 |
| 8,480,696 B2* | 7/2013 | Clague | ............ | A61B 17/00008 606/159 |
| 8,734,320 B2* | 5/2014 | Haarstad | ............ | A61B 17/0218 600/37 |
| 2003/0032973 A1* | 2/2003 | Jenusaitis | ......... | A61M 25/1027 606/192 |
| 2004/0138522 A1* | 7/2004 | Haarstad | ............ | A61B 17/0218 600/37 |
| 2005/0165432 A1* | 7/2005 | Heinrich | ............ | A61B 17/3417 606/167 |
| 2006/0079838 A1* | 4/2006 | Walker | ................ | A61M 25/04 604/104 |
| 2011/0152874 A1* | 6/2011 | Lyons | ................ | A61B 17/3415 606/108 |

* cited by examiner

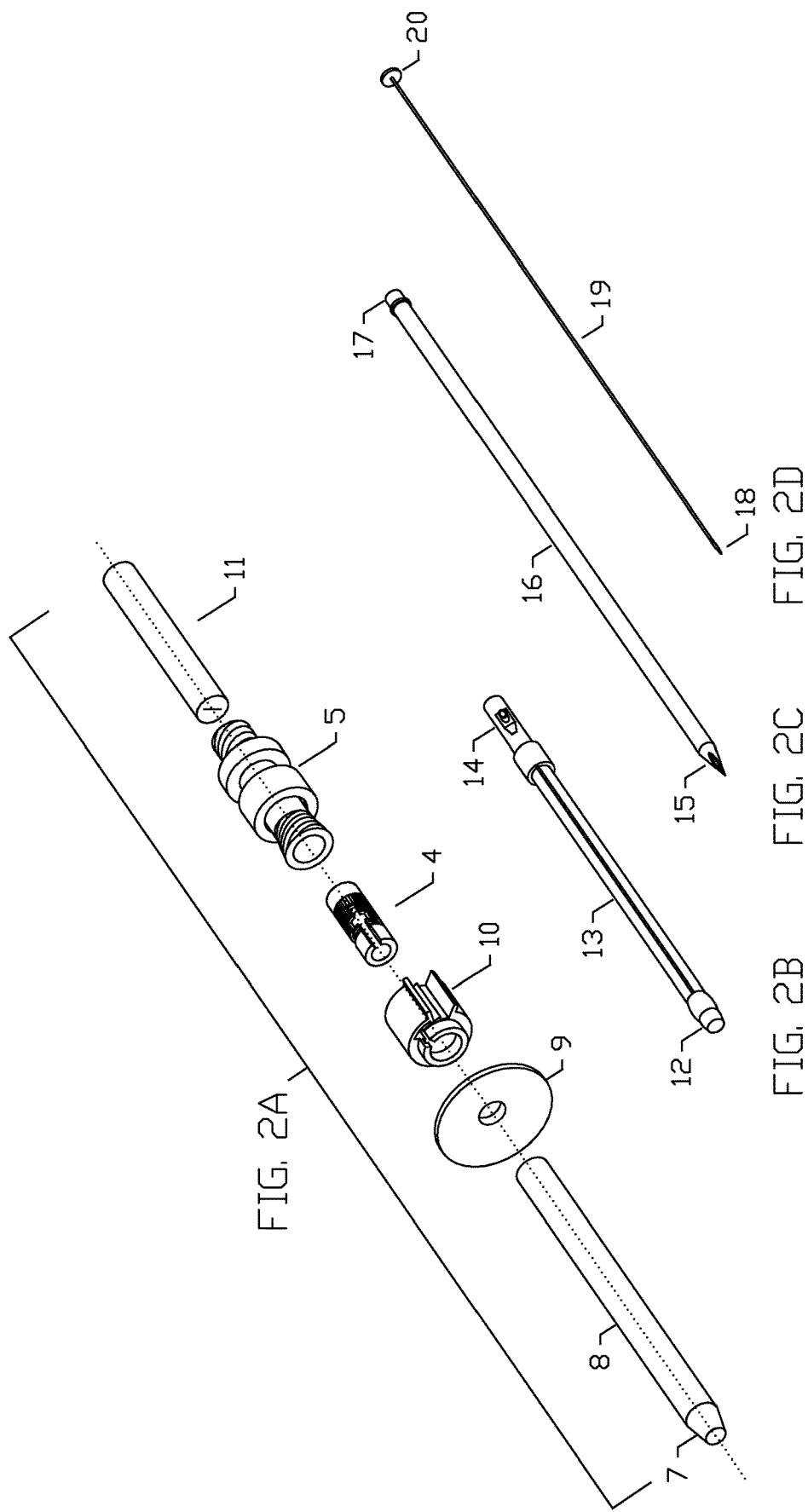

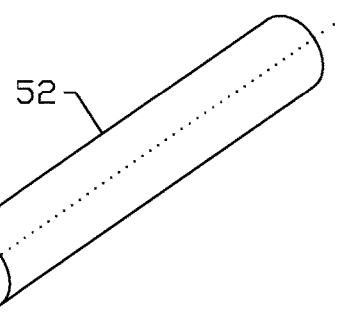
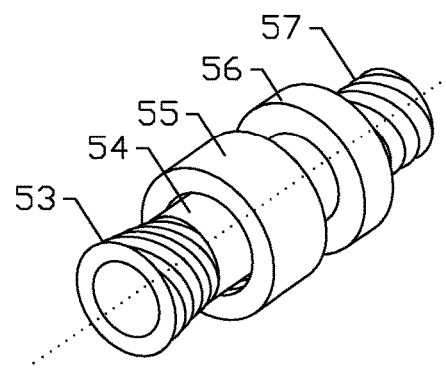
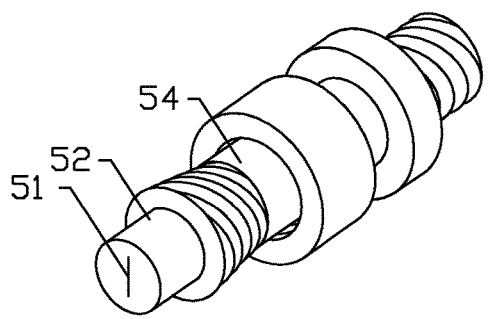
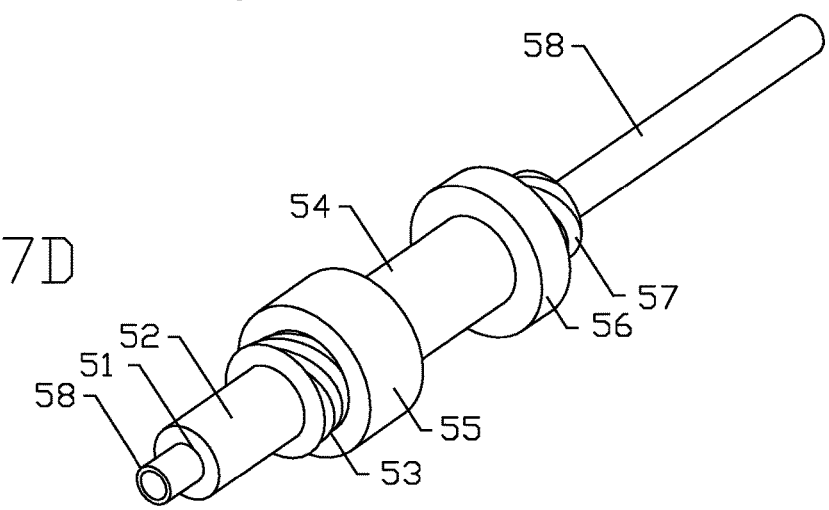
FIG. 7A
FIG. 7B
FIG. 7C
FIG. 7D

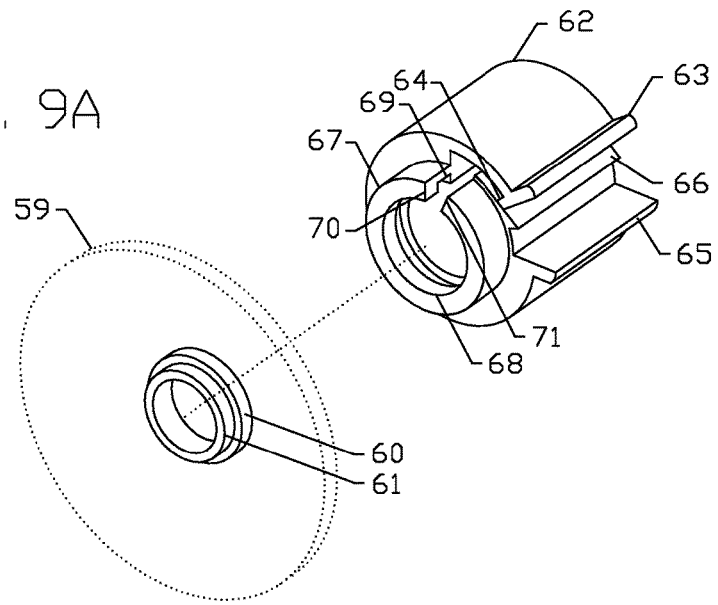
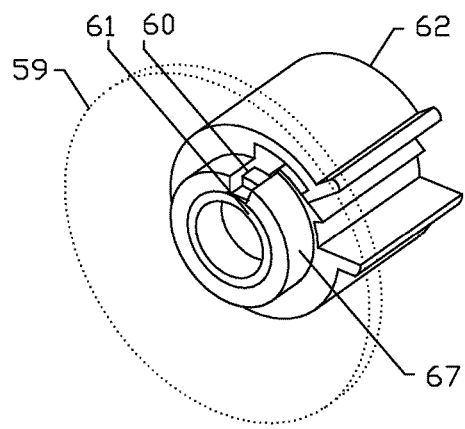
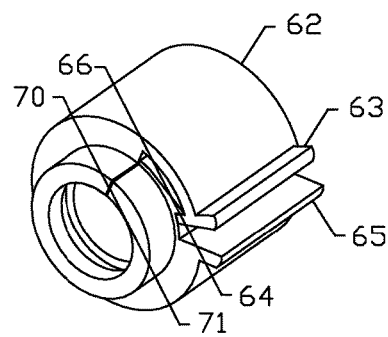
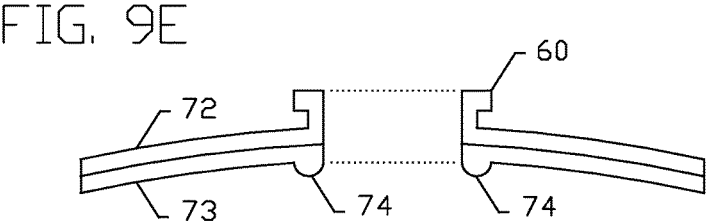

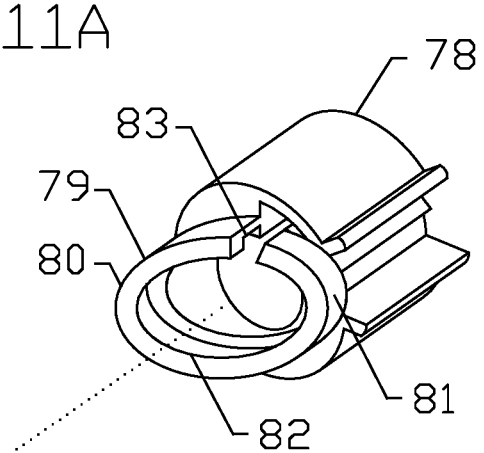
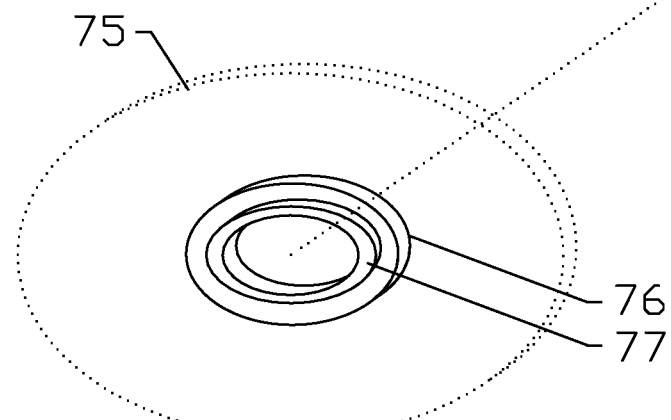
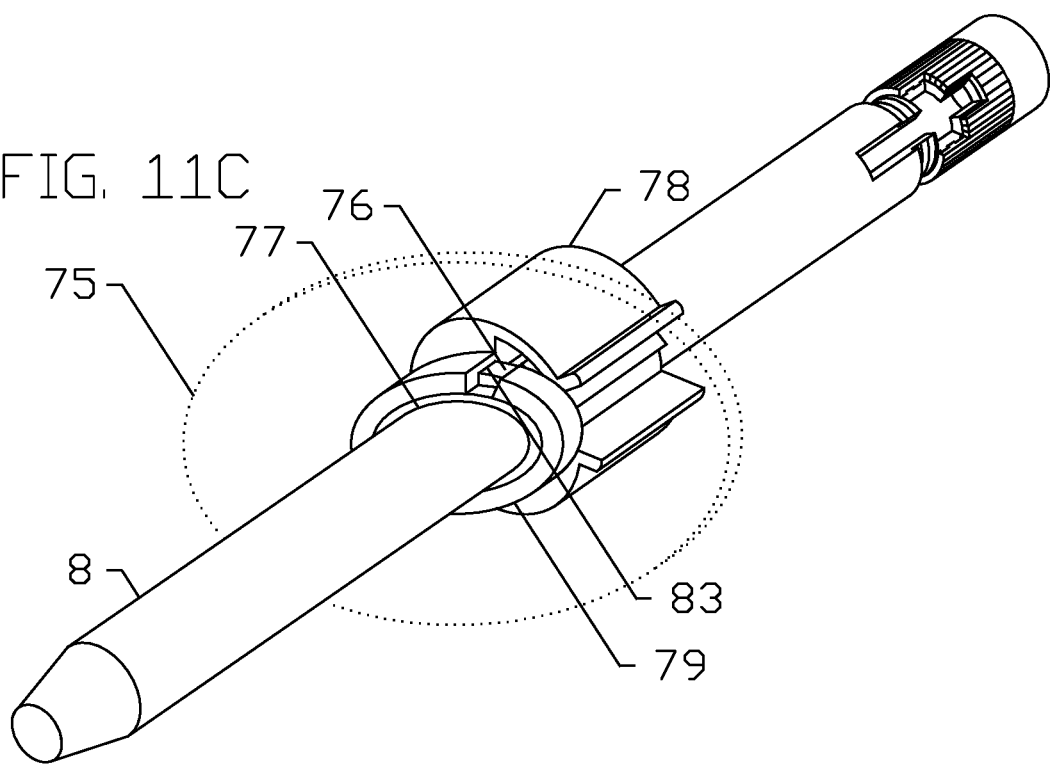

NON-SURGICAL CHEST TUBE INTRODUCER

CROSS REFERENCE TO RELATED APPLICATIONS

Attached please refer to the Information Disclosure Statement for the cross reference to related applications.

TECHNICAL FIELD

The present invention relates generally to the field of introducing a cannula to a chest cavity. More specifically, the present invention provides an apparatus for non-surgical introduction of a chest tube into a pleural space.

BACKGROUND OF THE INVENTION

Placement of a chest tube through a chest wall into a pleural cavity requires a surgical procedure whereby the chest wall is incised open under direct visualization. A main reason for this comes from a risk of inadvertent introduction of an ambient air into a chest cavity through an opening in the chest wall since a pressure in the pleural cavity is lower than that of the ambient air. In such a scenario, there comes a significant risk of collapse of a lung encased in the pleural cavity, which jeopardizes a main function of the lung of gas exchange. A second reason for the direct visualization is that an intercostal artery runs just below a rib along a lower lateral border, which could be severed by a blind procedure.

There are circumstances where surgical placement of the chest tube is impossible or impractical. In emergent situations away from a controlled medical environment and no available trained medical personnel for the placement of the chest tube, patient would run into a serious decision making of whether a tube of any kind should be inserted to save life or it would be necessary to take time for transfer to a medical facility. In a situation with a massive injury to multiple sites of body requiring coordinated resuscitative procedures, eliminating one surgical procedure for chest tube insertion would be advantageous for an overall management of patient. Cardiopulmonary resuscitation for a person having sustained multiple injuries would need to be interrupted for surgical procedures for chest tube insertion. A different scenario is for patients who would not be able to come to the medical facility including, for example, those on hospice care or those who are severely debilitated to a point he or she cannot be transferred to the medical facility.

A couple of key features of successful development of a chest tube introducer are prevention of inadvertent introduction of air into the pleural cavity by the chest tube introducer and control of penetration depth into the chest wall. Once the chest tube introducer is inserted into the pleural cavity, a chest tube is guided through the introducer into the pleural cavity. During insertion of the chest tube through the introducer to the pleural cavity, the ambient air can be sucked into the pleural cavity through inner openings of the chest tube introducer for the chest tube to pass through. It can be minimized if the inner openings of the chest tube introducer are arranged in a way each opening can be open and sealably closed separately from the other openings. The control of penetration depth can be accomplished by a slidable flange that can be reversibly fastened over the chest tube introducer. It is advantageous to have the chest tube and the chest tube introducer placed in an acute angle to a planar axis of the chest wall, which allows the chest tube and the chest tube introducer to be taped close to the chest wall. These two features can be combined in one configuration of a slidable flange for the present invention.

SUMMARY OF THE INVENTION

To provide an introducer configured to be inserted through a chest wall into a pleural cavity without a risk of air sucked into the pleural cavity, the present invention comprises an outer tube and a slidable inner tube in a tube-in-tube configuration having a series of air locking devices. The slidable inner tube is enclosably placed in and slidably movable inside the outer tube. A proximal portion of the outer tube is sealed internally for a circular space between the outer tube and the inner tube by an internal balloon disposed at a proximal portion of the slidable inner tube, which is configured to provide a proximal air lock between the outer tube and the slidable inner tube. A distal portion of the outer tube comprises a series of rotatable air lock devices arranged in tandem, through which a catheter or a tube passes toward a proximal portion of the slidable inner tube. A distal tube fastener is fixedly attached distally to a distal end of the outer tube, which is encircled by a pair of rotatable screw-caps. The distal tube fastener has an internal cylindrical bar having an inner longitudinal conduit which is configured to let a catheter or a tube pass through the inner longitudinal conduit and to sealably fasten the catheter or the tube. An elastomeric ring is provided around the distal portion of the slidable inner tube, which fixedly encircles the distal portion of the slidable inner tube and is slidable inside the outer tube, which is configured to provide a distal air lock between the outer tube and the slidable inner tube. A rotatable reversible air lock is disposed at the distal portion of the outer tube proximal to a proximal end of the distal tube fastener, which is configured to rotatably lock the elastomeric ring of a distal end of the slidable inner tube inside the distal portion of the outer tube.

In one embodiment to control an insertion depth of the introducer into the chest wall, the introducer comprises a slidable flange and a slidable tube fastener, which encircle the outer tube and are configured to slide over the outer tube. The slidable tube fastener is configured to circumferentially fasten the slidable outer flange to the outer tube at an acute angle. The introducer is configured to get securely anchored inside the pleural cavity by the internal balloon of the slidable inner tube in a distended configuration, and to the chest wall by the slidable tube fastener fastening the outer tube in place.

In one embodiment, the introducer comprises a trocar which runs longitudinally from a distal end of the inner longitudinal conduit of the distal fastener through a proximal end of the slidable inner tube inside the inner longitudinal conduit of the distal fastener and the slidable inner tube. The trocar comprises a sharpened tip at a proximal end of the trocar, a hub at a distal end of the trocar and a shaft having a central tubular lumen in which a cylindrical stylet is slidably placed. The shaft is connected to the tip proximally and to the hub distally. The hub is configured to mate with a connecting tube of a syringe. The trocar and the cylindrical stylet are made of steel and are configured to be flexible. The trocar and the cylindrical stylet are configured to serve to stiffen the introducer in a way the introducer can be inserted to the pleural cavity through the chest wall by directional pressure from a distal portion of the introducer to a proximal portion of the introducer. Once the proximal portion of the introducer has penetrated into the pleural cavity, the cylindrical stylet is taken out from the trocar through the hub of the trocar and the syringe is connected to the hub of the trocar to confirm a location of the proximal portion of the introducer by suctioning materials from the pleural cavity.

In one embodiment, the slidable inner tube comprises the proximal portion having the internal balloon disposed at the proximal portion, the distal portion having an intake hub disposed at the distal portion at a right angle to a longitudinal axis of the slidable inner tube, and a tubular shaft having a pair of sliding rails longitudinally disposed on an outer surface of the tubular shaft. The tubular shaft is connected to the proximal portion proximally and to the distal portion distally. The sliding rails are configured to mate with a pair of corresponding slots longitudinally disposed on an inner surface of the outer tube. One of the sliding rails has a central tubular lumen disposed longitudinally in a center of the sliding rail, which is connected to the internal balloon proximally and to the intake hub distally. The longitudinal central tubular lumen is configured to serve as conduit between the intake hub and the internal balloon.

In one embodiment, the proximal portion of the slidable inner tube comprises a tip which adjoins distally the tubular shaft of the slidable inner tube and the internal balloon adherently disposed at the proximal portion of the slidable inner tube circumferentially on the outer surface of the tubular shaft of the slidable inner tube. The tip is configured to protrude proximally for a length from a proximal border of the internal balloon. A distal portion of the tip and the internal balloon are configured to be enclosably housed inside the proximal portion of the outer tube and to be slid out forward from the proximal portion of the outer tube by forward sliding movement of the slidable inner tube inside the outer tube. A proximal portion of the tip of the proximal portion of the slidable inner tube is configured to protrude for a length beyond a proximal end of the outer tube in an unengaged configuration and to enclosably cover a part of the tip of the trocar.

In one embodiment, the circular space between the proximal portion of the outer tube and the proximal portion of the slidable inner tube enclose the distal portion of the tip of the proximal portion of the slidable inner tube and the internal balloon. The internal balloon enclosed inside is maintained partially inflated to an extent to seal the circular space in the unengaged configuration and to let the inflated internal balloon squeezably pass through a circular opening of the outer tube disposed at the proximal end of the outer tube upon the forward sliding movement of the slidable inner tube inside the outer tube. Once the partially-inflated internal balloon is advanced forward out of the proximal end of the outer tube, the inflated internal balloon is configured to be inflated further by insufflation of a gas through the intake hub of the slidable inner tube. A fully inflated internal balloon is configured to securely position the introducer inside the pleural cavity.

In one embodiment, the distal tube fastener comprises a fastenable outer tube and the internal cylindrical bar disposed inside the fastenable outer tube. The fastenable outer tube comprises a first helically threaded portion on a proximal portion of the fastenable outer tube and a second helically threaded portion on a distal portion of said fastenable outer tube. A proximal end of the proximal portion of the fastenable outer tube fixedly adjoins the distal end of the outer tube. A proximal end of the internal cylindrical bar of the distal tube fastener adjoins the distal end of the slidable inner tube. The inner longitudinal conduit of the internal cylindrical bar is coaxially aligned with the longitudinal axis of the slidable inner tube. The internal cylindrical bar is configured to slide to and fro inside the fastenable outer tube and to be locked by tightening the rotatable screw-caps around the first and the second helically threaded portions of the fastenable outer tube. A first rotatable screw-cap has clockwise inner helical threads on an inner surface of the first rotatable screw-cap, and a second screw-cap has clockwise inner helical threads on an inner surface of the second rotatable screw-cap similar to the first screw-cap. The inner helical threads of the screw-cap are configured to mate with the helically threaded portion of the fastenable outer tube.

In one embodiment, the internal cylindrical bar is made of an elastomer such as silicone rubber. Along a longitudinal axis of the internal cylindrical bar, there is provided a longitudinal slit running from one end to the other end of the internal cylindrical bar inside the internal cylindrical bar. The slit is configured to be closed in an unengaged configuration and to be widened to a round configuration upon introduction of a tube or a catheter into the slit. The helically threaded portion of the fastenable outer tube of the distal tube fastener is configured to concentrically squeeze and lock the internal cylindrical bar by tightening the rotatable screw-cap around the helically threaded portion. Reversing the tightened rotatable screw-cap from the helically threaded portion is configured to release the internal cylindrical bar from the helically threaded portion.

In one embodiment, the intake hub of the slidable inner tube is configured to take off at an angle from the distal portion of the slidable inner tube and to protrude for a length through an opening disposed at the distal portion of the outer tube on a tubular wall of the outer tube. The intake hub is configured in a cylindrical tube with an one-way valve located inside the cylindrical tube closing the cylindrical tube in an unengaged configuration. The intake hub is configured to couple with a tip of a syringe which provides the intake hub with gas or liquid so as to inflate the internal balloon. The one-way valve of the intake hub is configured to be pushed open by the tip of the syringe. The intake hub is configured to be used as a handle of the slidable inner tube, so as to slide the slidable inner tube inside the outer tube. A forward sliding of the slidable inner tube is configured to advance the tip and the internal balloon of the slidable inner tube out of the proximal end of the outer tube. A backward sliding of the slidable inner tube is configured to retrieve the tip and the internal balloon back inside the proximal portion of the outer tube.

In one embodiment, the distal portion of the outer tube comprises the rotatable reversible air lock having the opening of the distal portion of the outer tube and an outer rotatable screw-cap disposed distal to the opening on an outer surface of the distal portion of the outer tube. The opening of the distal portion of the outer tube is provided as a perforated space in a rectangular configuration on the tubular wall of the outer tube, having a proximal portion and a distal portion along the longitudinal axis of the outer tube. The opening is configured to accommodate forward and backward sliding movements of the intake hub of the slidable inner tube. The intake hub is placed in the distal portion of the opening in the unengaged configuration of the introducer, and is slidably movable proximally to the proximal portion of the opening to advance the tip and the internal balloon of the slidable inner tube out of the proximal end of the outer tube. The opening is configured to be reversibly closable by the outer rotatable screw-cap which is configured with internal helices to mate with a helically threaded portion disposed on the outer surface of the distal portion of the outer tube. The helically threaded portion of the distal portion of the outer tube is located in front of the fastenable outer tube of the distal tube fastener. The outer rotatable screw-cap axially rotates about the outer surface of the distal portion of the outer tube to close the distal portion of the opening once the intake hub is moved to the proximal portion of the opening, and to lock the intake hub in the proximal portion of the opening. The outer rotatable screw-cap is configured to air-tightly close the opening, and the opening is configured to provide a leakproof seal around a border between the opening and the intake hub of the slidable inner tube.

In one embodiment, the slidable flange of the introducer comprises a circular disk having a central hole, and a connecting circular ridge encircling the central hole. The slidable flange is slidably placed over the outer tube. A first planar surface of the circular disk having the connecting circular ridge faces the distal portion of the outer tube, and a second planar surface of the circular disk opposite to the first planar surface faces the proximal portion of the outer tube and is configured to contact the chest wall. The second planar surface is configured with an adhesive for adhering to a skin of the chest wall. The adhesive is provided in a leakproof configuration to seal off a penetrated area of the chest wall by the introducer. The connecting circular ridge is configured to mate with a circular slot disposed on an inner surface of a connecting circular rim clamp of the slidable tube fastener. The slidable tube fastener comprises the connecting circular rim clamp and a tubular clamp fixedly and coaxially adjoining the connecting circular rim clamp along a longitudinal axis of the slidable tube fastener. The connecting circular rim faces the proximal portion of the outer tube, and the tubular clamp faces the distal portion of the outer tube. The slidable tube fastener is connected with the slidable flange by mating the connecting circular ridge of the slidable flange with the connecting circular rim clamp of the slidable tube fastener. The slidable tube fastener is configured to slide over the outer tube in an un-clamped configuration, and to reversibly fasten to the outer tube in a clamped configuration.

In one embodiment, a chest wall of a patient is sterilized and given a local anesthetics if available around a site of introduction of the introducer. A tip of a trocar of a new introducer in an unengaged configuration having the trocar and a stylet inside a slidable inner tube which is enclosed by an outer tube is placed on an intercostal space of the chest wall. A slidable flange assembled with a slidable tube fastener in an unclamped configuration is grabbed together with a shaft of the outer tube by an operator's hand at a position over the outer tube for a necessary length of tissue of the chest wall to be penetrated through to get into a pleural cavity. A distal end of the introducer is manually pushed forward so as to make the tip of the introducer penetrate through the chest wall into a pleural cavity. Once the slidable flange assembled with the slidable tube fastener is pushed against the chest wall, a tubular clamp of the slidable tube fastener is clamped to fixate the position. The stylet is withdrawn from a distal end of the trocar. A syringe hub of a first syringe is connected to a corresponding hub of the distal end of the trocar, and a plunger of the first syringe is withdrawn to retrieve any materials from the pleural cavity. Once intrapleural materials are withdrawn, thereby confirming a location of a proximal portion of the introducer in the pleural cavity, an intake hub of the slidable inner tube is slidably advanced forward inside an opening of a distal portion of the outer tube, so as to advance forward an internal balloon out of the outer tube into the pleural cavity. Following the forward placement of the intake hub in the opening of the outer tube, a syringe hub of a second syringe is connected to the intake hub of the slidable inner tube. The second syringe then is used to fully inflate the internal balloon of the slidable inner tube by insufflating a predetermined volume of gas into the internal balloon. Once the internal balloon is fully distended, thereby anchoring the proximal portion of the introducer inside the pleural cavity, the trocar is removed from a distal end of a distal tube fastener of the outer tube. The slidable flange and the slidable tube fastener are readjusted for their position over the outer tube in order to establish a tight placement of the introducer to the chest wall. Following the tight placement of the introducer to the chest wall, a chest tube or an intrapleural catheter is inserted through the distal tube fastener into the pleural cavity. After proper placement of a tip of the chest tube or the intrapleural catheter, the chest tube or the intrapleural catheter is fixated inside the distal tube fastener by tightening the distal tube fastener by rotatable screw-caps.

BRIEF DESCRIPTION OF THE DRAWINGS

FIGS. 2A-2D represent a schematic view of individual components of the introducer; FIG. 2A shows a schematic view of an outer tube assembly; FIG. 2B shows a schematic view of a slidable inner tube assembly; FIG. 2C shows a schematic view of a trocar; FIG. 2D shows a schematic view of a stylet.

FIG. 6A shows a schematic view of the tip and the internal balloon of the slidable inner tube assembly in an unengaged configuration; FIG. 6B shows a schematic view of the tip and a proximal portion of the internal balloon being squeezably advanced through out of a proximal opening of the outer tube assembly; FIG. 6C shows a schematic view of the tip and the internal balloon of the slidable inner tube assembly fully advanced out of the proximal opening of the outer tube assembly.

FIGS. 7A-7D show schematic views of a distal tube fastener assembly and an internal cylindrical bar.

FIG. 8A shows a schematic view of the outer tube assembly having the slidable inner tube assembly in the unengaged configuration; FIG. 8B shows a schematic view of the slidable inner tube assembly fully advanced forward inside the outer tube assembly; FIG. 8C shows the internal balloon in an inflated configuration.

FIGS. 9A-9E show schematic views of a slidable tube fastening assembly comprising a slidable flange and a slidable tube faster.

FIGS. 11A-11C show schematic views of an angled slidable flange and an angled slidable tube fastener, and their placement over the outer tube assembly.

DETAILED DESCRIPTION OF THE DRAWINGS

As described below, the present invention provides a mechanical-waves dissipating protective headgear apparatus. It is to be understood that the descriptions are solely for the purposes of illustrating the present invention, and should not be understood in any way as restrictive or limited. Embodiments of the present invention are preferably depicted with reference to FIGS. 1 to 12, however, such reference is not intended to limit the present invention in any manner. The drawings do not represent actual dimension of devices, but illustrate the principles of the present invention.

Figure 1:
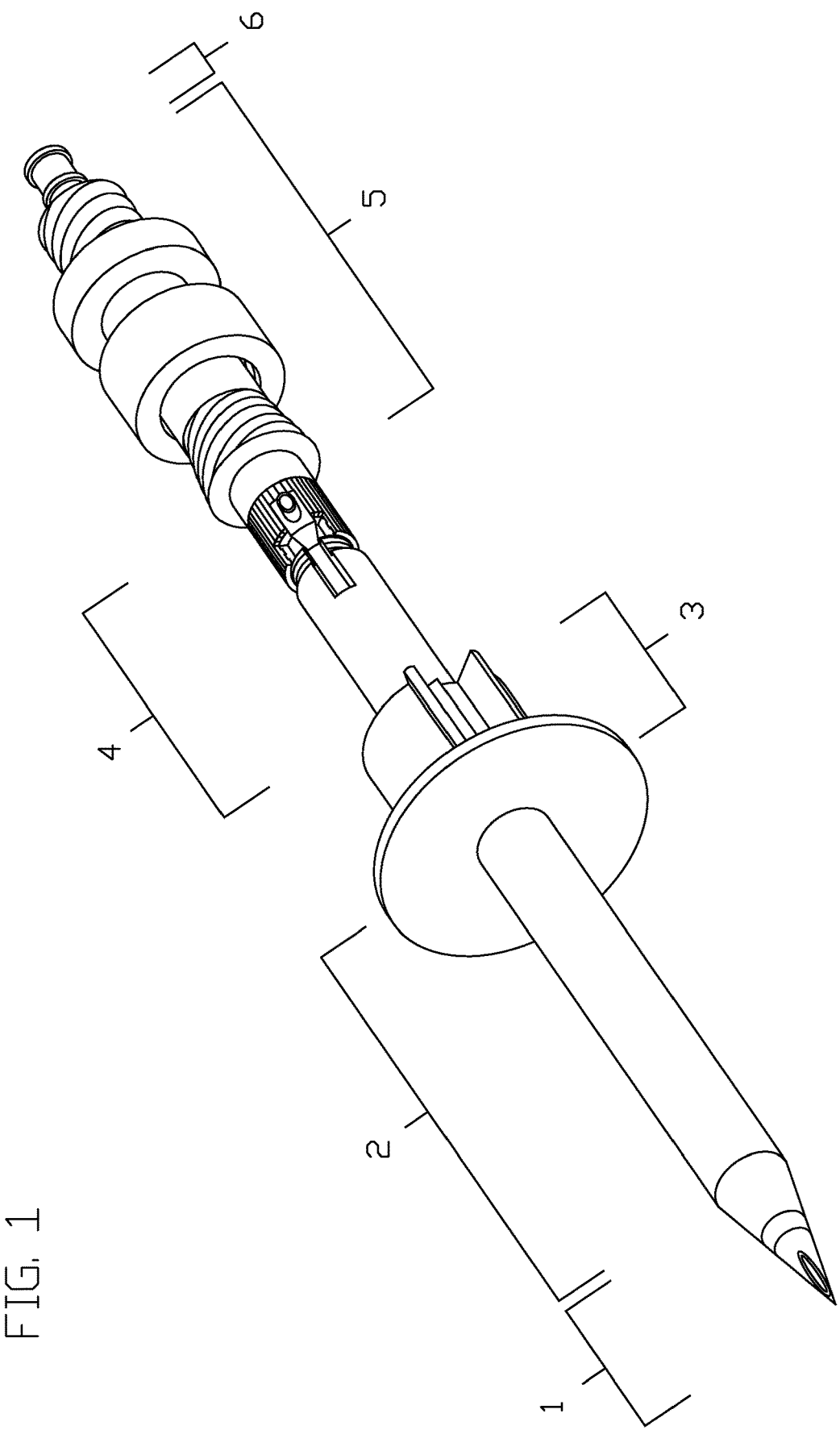
FIG. 1 shows a schematic presentation of an introducer for a chest tube or a catheter.

FIG. 1 shows a schematic presentation of an introducer comprising in tandem a proximal portion 1, a mid portion 2, a slidable tube fastening assembly 3, a rotatable reversible air lock assembly 4, a distal tube fastener assembly 5, and a distal end 6. The proximal portion 1 is configured to penetrate a chest wall into a pleural cavity, and to prevent air leakage into the pleural cavity through the introducer. The slidable tube fastening assembly 3 is configured to slide over the mid portion 2 along a longitudinal axis of the mid portion 2, and to fasten the introducer to the chest wall. The rotatable reversible air lock assembly 4 is configured to reversibly and sealably lock a distal portion of a slidable inner tube assembly disposed inside the rotatable reversible air lock assembly 4. The distal tube fastener assembly 5 is configured to reversibly and sealably lock a chest tube or a catheter disposed inside the distal tube fastener 5.

FIGS. 2A-2D represent a schematic view of individual components of the introducer. FIG. 2A shows a schematic view of an outer tube assembly which comprises a proximal portion 7 in a tapered conical configuration, a mid tubular shaft 8, the rotatable reversible air lock assembly 4, and the distal tube fastener assembly 5, and an internal cylindrical bar 11. A slidable flange 9 and a slidable tube fastener 10 of the slidable tube fastening assembly are configured to slide over the mid tubular shaft 8 of the outer tube assembly. FIG. 2B shows a schematic view of a slidable inner tube assembly which comprises a proximal portion 12 in a tapered conical configuration, a mid tubular shaft 13, and a distal portion 14. The proximal portion 12 of the slidable inner tube assembly is configured to slidably disposed inside the proximal portion 7 of the outer tube assembly, the mid tubular shaft 13 is slidably disposed inside the mid tubular shaft 8 of the outer tube assembly, and the distal portion 14 of the slidable inner tube assembly is configured to be disposed inside the rotatable reversible air lock assembly 4 and to couple with the rotatable reversible air lock assembly 4 of the outer tube assembly of FIG. 2A. A proximal end of the internal cylindrical bar 11 of the outer tube assembly of FIG. 2A is configured to fixedly adjoin a distal end of the distal portion 14 of the slidable inner tube assembly. FIG. 2C shows a schematic view of a trocar comprising a tip portion 15, a mid tubular shaft 16, and a distal hub 17. The trocar is configured to be inserted in the internal cylindrical bar of the distal tube fastener assembly 5 of FIG. 2A and the slidable inner tube assembly of FIG. 2B. FIG. 2D shows a schematic view of a stylet comprising a tip 18, a mid shaft 19, and a distal end 20. The stylet is configured to be inserted in the trocar of FIG. 2C. The proximal portion 1 of the introducer of FIG. 1 comprises the tip 18 of the stylet of FIG. 2D slidably placed in the tip portion 15 of the trocar of FIG. 2C which in turn is slidably placed in the proximal portion 12 of the slidable inner tube assembly of FIG. 2B.

Figure 3A:
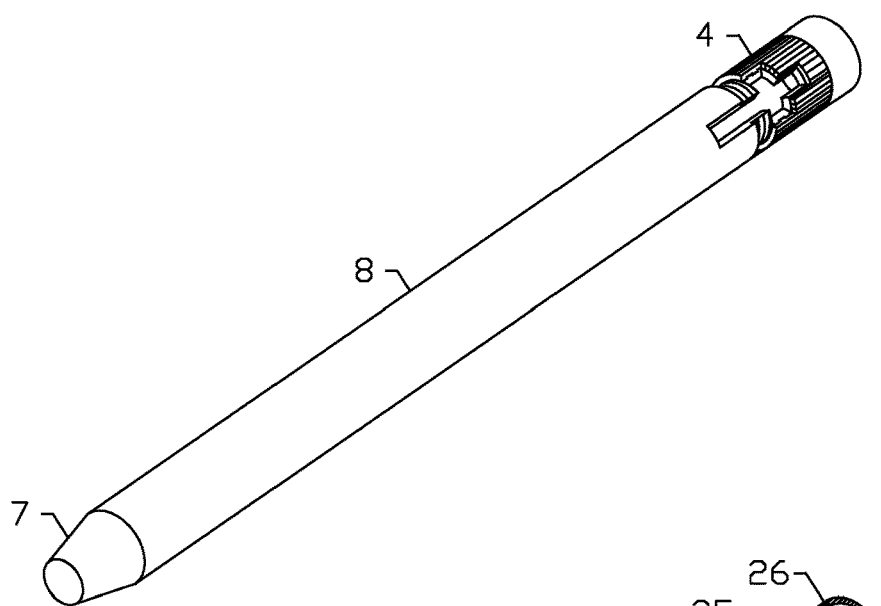
FIGS. 3A-3D illustrate a schematic view of part of the outer tube assembly.
Figure 3B:
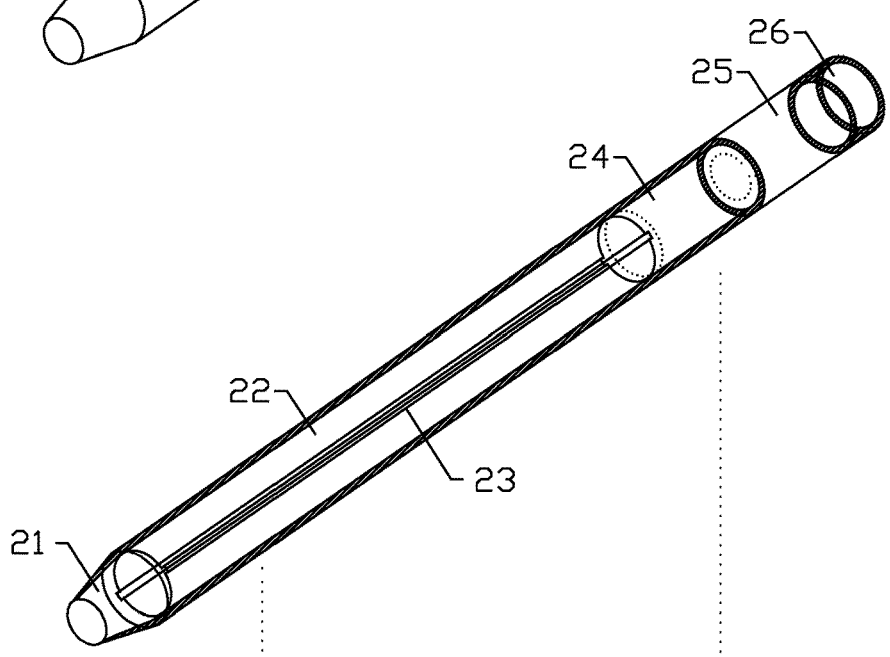
Figure 3C:
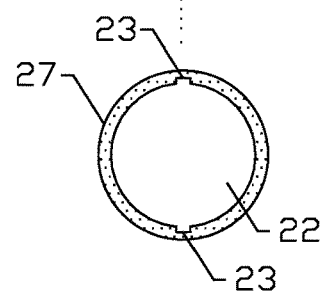
Figure 3D:
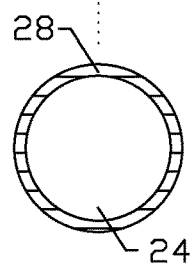

FIG. 3A illustrates a schematic view of part of the outer tube assembly having the proximal portion 7 and the mid tubular shaft 8 adjoining the rotatable reversible air lock assembly 4. FIG. 3B shows a schematic see-through three-dimensional view of the part of the outer tube assembly, comprising a conical space 21 inside the proximal portion 7, a mid tubular space 22, a couple of linear sliding slots 23 disposed on an inner surface of the mid tubular shaft 8, first and second distal tubular spaces 24 and 25 configured to accommodate the distal portion 14 of the slidable inner tube assembly of FIG. 2B, and a third distal tubular space 26 configured to accommodate a proximal portion of the internal cylindrical bar 11 of FIG. 2A. FIG. 3C shows a schematic cross-sectional view of the mid tubular shaft 8 of FIG. 2A, comprising a pair of sliding slots 23 opened to the mid tubular space 22 and carved in the inner surface of a tubular wall 27. FIG. 3D shows a schematic cross-sectional view of the first distal space 24 encircled by a wall 28 which does not have the pair of the sliding slots.

Figure 4A:
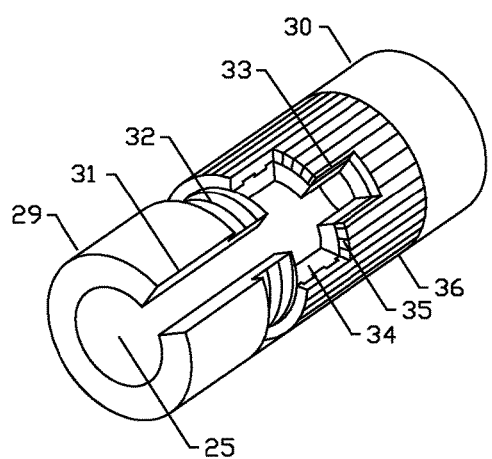
FIGS. 4A-4D depict a schematic view of a rotatable reversible air lock assembly disposed at a distal portion of the outer tube assembly.
Figure 4B:
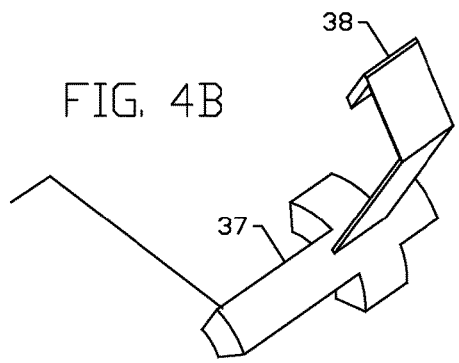
Figure 4C:
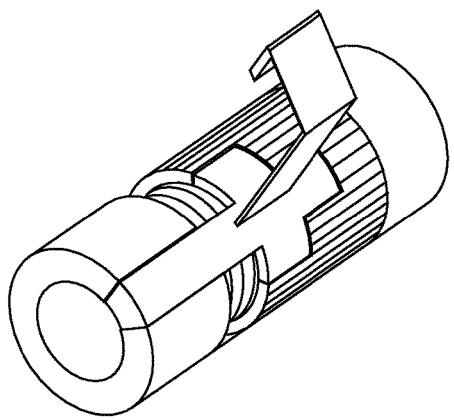
Figure 4D:
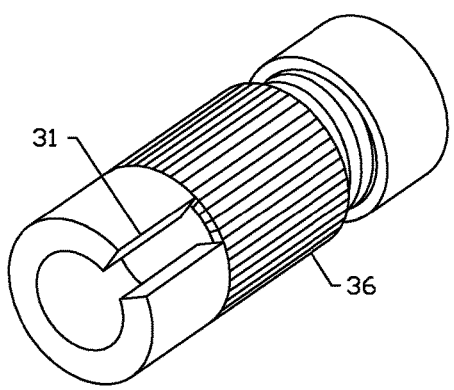

FIG. 4A depicts a schematic view of the rotatable reversible air lock assembly disposed thereof at the distal portion of the outer tube assembly, comprising in tandem a proximal tubular portion 29, a helically threaded portion 32, and a distal tubular portion 31. The proximal tubular portion 29 has a proximal linear open slot 31 disposed longitudinally on a tubular wall of the proximal tubular portion. The helically threaded portion 32 comprises a linear open slot in linear continuity with the proximal linear open slot 31, a rectangular open space 34 disposed on a threaded wall of the helically threaded portion in a cross configuration in relation to the proximal linear open slot 31, and a distal linear open slot 33 in linear continuity with the rectangular open space 34 and the proximal linear open slot 31. A rotatable screw-cap 36 having a corresponding rectangular open space 35 to the rectangular open space 34 is configured to encircle the helically threaded portion 32 and to helically and reversibly cover and lock the distal linear open slot 33 and the rectangular open space 34. In an unengaged configuration of the rotatable reversible air lock assembly, the proximal and distal linear open slots 31 and 33 and the rectangular open space 34 of the rotatable reversible air lock assembly are detachably covered by a plug as shown in FIG. 4B. The plug comprises a knob 38 and a main body 37 for plugging the proximal and distal linear open slots 31 and 33 and the rectangular open space 34, as shown in FIG. 4C. FIG. 4D shows the rotatable screw-cap 36 fully covering and locking the distal linear open slot 33 and the rectangular open space 34 of the helically threaded portion of FIG. 4A, while leaving the proximal linear open slot 31 open.

Figure 5A:
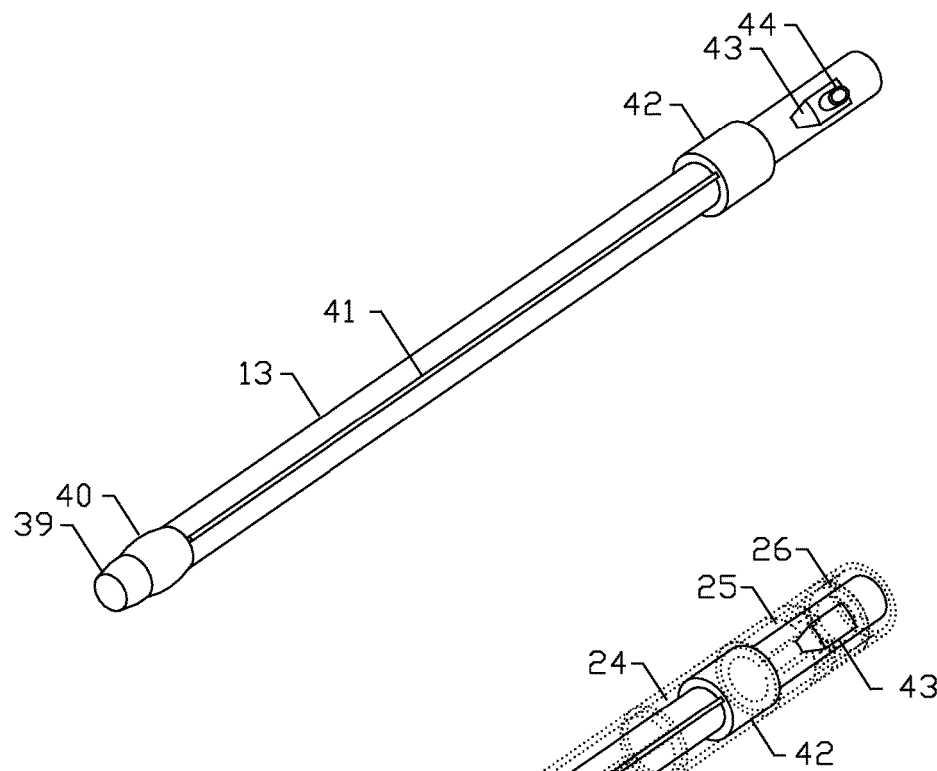
FIGS. 5A-5D show a schematic illustration of the slidable inner tube assembly.
Figure 5B:
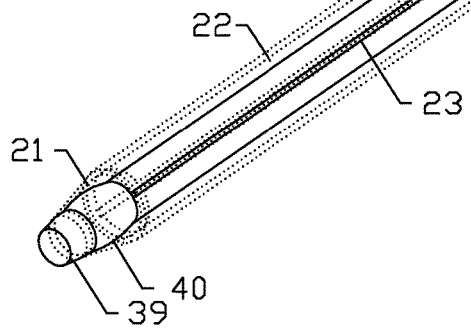
Figures 5C, 5D:
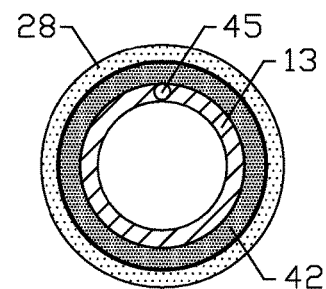

FIGS. 5A-5D show a schematic illustration of the slidable inner tube assembly comprising a proximal tubular portion 39 provided in a conical configuration, and an internal balloon 40 encircling a proximal part of the mid tubular shaft 13. The internal balloon 40 is disposed distal to the proximal tubular portion 39 and is communicated with an intake hub 44 of an intake hub assembly located thereof at the distal portion of the slidable inner tube assembly via an internal conduit 45 which runs longitudinally inside a sliding rail 41 disposed on an outer surface of the slidable inner tube assembly. The intake hub 44 of the intake hub assembly is connected via a neck portion 43 of the intake hub assembly to the distal portion of the slidable inner tube assembly. Proximal to the intake hub 44, there is provided an elastomeric ring 42 of the intake hub assembly which fixedly encircles an outer surface of a distal part of the mid tubular shaft 13, and is configured to air-lock the first and the second distal tubular spaces 24 and 25. The elastomeric ring 42 of the intake hub assembly is configured to be slidably movable back and forth inside the first and the second distal tubular spaces. The sliding rail 41 is configured to couple with the sliding slot 23 disposed on the inner surface of the mid tubular shaft wall 27 of the outer tube assembly as shown in FIG. 3C. The internal balloon 40 of the slidable inner tube assembly is located inside the conical space 21 of the outer tube assembly in an unengaged configuration. A tip of the proximal tubular portion 39 is configured to protrude a proximal end of the conical space 21 in the unengaged configuration. FIG. 5C shows a cross-sectional view of a couple of the sliding rails 41 coupled with each corresponding sliding slot 23. FIG. 5D shows a cross-sectional layout of the elastomeric ring sealably located in between the outer tubular wall 28 and the mid tubular shaft wall 13.

Figure 6A:
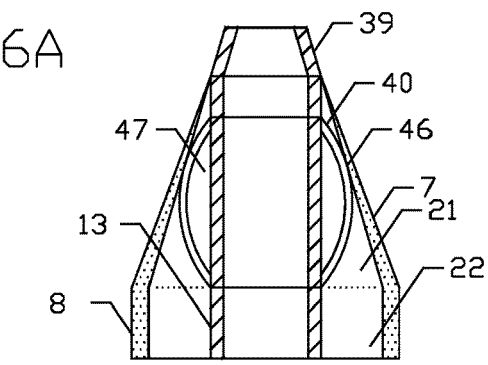
FIGS. 6A-6C show schematic coronal views of a tip and an internal balloon of the slidable inner tube assembly inside a proximal portion of the outer tube assembly.
Figure 6B:
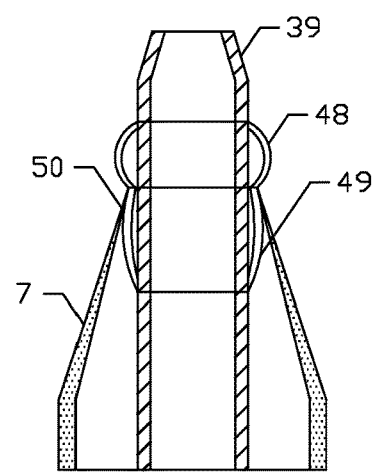
Figure 6C:
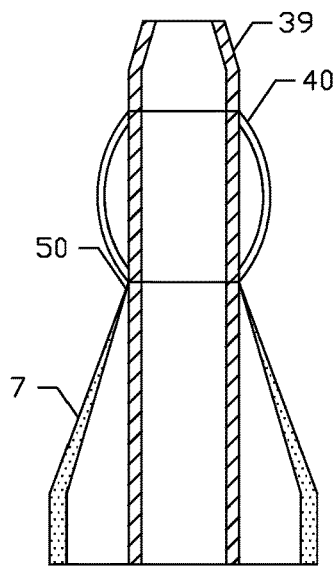

FIG. 6A show a schematic coronal view of a placement of the proximal portion of the slidable inner tube assembly inside the conical space 21 of the outer tube assembly. The conical space 21 is encircled by a tapered wall of the proximal portion 7 of the outer tube assembly, which is connected to the mid tubular space 22 formed by the mid tubular shaft 8. The tip of the proximal tubular portion 39 of the slidable inner tube assembly is protruded outside from the proximal end of the proximal portion 7 of the outer tube assembly, and the internal balloon 40 remains inside the conical space 21 of the outer tube assembly in the unengaged configuration. The internal balloon 40 is partially inflated to a size 47 to fill the conical space 21 with an outer wall 46 of the internal balloon 40 touching an inner surface of the conical space 21, thereby internally sealing the conical space for air-locking. In FIG. 6B, the tip of the proximal tubular portion 39 and a proximal portion of the internal balloon 40 are being squeezably advanced through the proximal end of the proximal portion 7 of the outer tube assembly. The internal balloon 40 is squeezed to get divided by the proximal end 50 of the outer tube assembly into a proximal portion 48 and a distal portion 49 which yet remains inside the conical space 21. This configuration assures of a tight air-lock between the slidable inner tube assembly and the outer tube assembly during forward sliding movement of the slidable inner tube assembly inside the outer tube assembly. As shown in FIG. 6C, Once pushed forward to the full extent, the internal balloon 40 of the slidable inner tube assembly is fully out of the proximal end 50 of the outer tube assembly and is ready to be inflated.

FIGS. 7A-7D show schematic views of a distal tube fastener assembly. FIG. 7A shows the internal cylindrical bar 11 of FIG. 2A comprising a cylindrical bar 52 and a central longitudinal slit 51 axially placed in the cylindrical bar along full length of the cylindrical bar. The cylindrical bar is made of an elastomer which allows the central longitudinal slit to close in an unengaged configuration and to be reversibly widened upon insertion of a longitudinal catheter or a tube. Closed configuration of the cylindrical bar prevents air leakage through the central longitudinal slit. FIG. 7B shows the distal tube fastener assembly comprising a proximal tubular portion 53 having an outer helical thread, a distal tubular portion 57 having an outer helical thread, and a mid tube 54 connecting the proximal tubular portion 53 to the distal tubular portion 57. The proximal tubular portion 53 is provided in a tapered configuration with a larger tubular size of a proximal end of the proximal tubular portion than that of a distal end of the proximal tubular portion. The distal tubular portion 57 is provided in a tapered configuration with a larger tubular size of a distal end of the distal tubular portion than that of a proximal end of the distal tubular portion. First screw-cap 55 having a corresponding thread to mate with the outer helical thread of the proximal tubular portion 53 is slidably placed over the outer helical thread of the proximal tubular portion 53, and second screw-cap 56 having a corresponding thread to mate with the outer helical thread of the distal tubular portion 57 is slidably placed over the outer helical thread of the distal tubular portion 57. The cylindrical bar 52 is configured to be slidably and movably placed inside a tubular lumen of the distal tube fastener assembly, as shown in FIG. 7C. A full engaged configuration of the distal tube fastener assembly having a catheter 58 inserted inside the central longitudinal slit 51 in an open configuration is shown in FIG. 7D. The cylindrical bar 52 is advanced forward and is tightened for leakproof immobilization inside the distal tube fastener by the first screw-cap 55 tightening the proximal tubular portion 53 and by the second screw-cap 56 tightening the distal tubular portion 57.

Figure 8A:
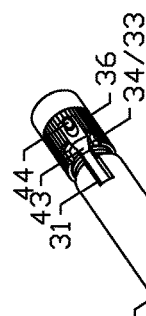
FIGS. 8A-8C show schematic sequential views of the slidable inner tube assembly advancing forward inside the outer tube assembly.
Figure 8B:
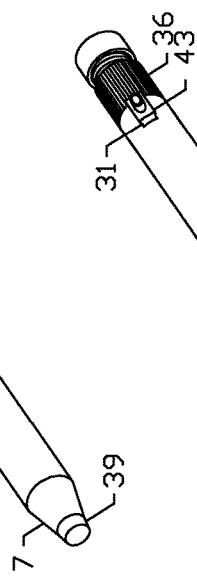
Figure 8C:
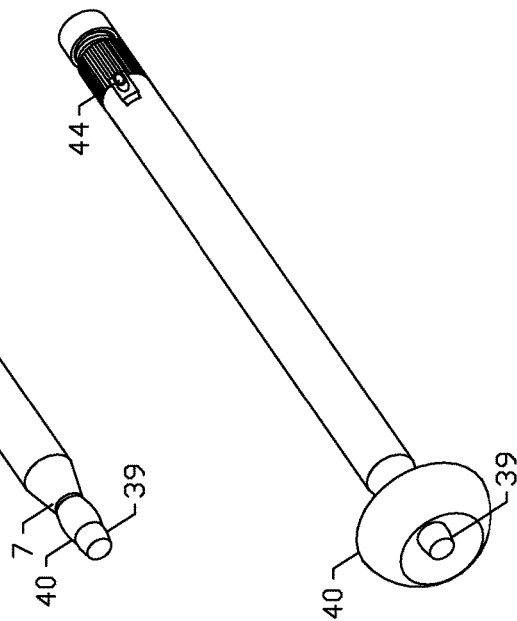

FIGS. 8A-8C show schematic sequential views of the slidable inner tube assembly advancing forward inside the outer tube assembly. FIG. 8A shows a schematic view of the outer tube assembly having the slidable inner tube assembly in the unengaged configuration. The tip of the proximal tubular portion 39 of the slidable inner tube assembly is protruded outside from the proximal end of the proximal portion 7 of the outer tube assembly. The neck portion 43 of the intake hub 44 to the distal portion of the slidable inner tube assembly having the intake hub 44 is slidably inserted in and protruded from the distal linear open slot 33 and the rectangular open space 34 of the rotatable reversible air lock assembly disposed distal to the mid tubular shaft 8 of the outer tube assembly. As shown in FIG. 8B, the neck portion 43 is slidably advanced forward to the proximal linear open slot 31 of the outer tube assembly and is locked by the rotatable screw-cap 36. With the forward advance of the neck portion 43 of the slidable inner tube assembly, the proximal tubular portion 39 of the slidable inner tube assembly and the internal balloon 40 are pushed out from the proximal portion 7 of the outer tube assembly. As shown in FIG. 8C, the internal balloon 40 is inflated further by insufflating an air or a liquid through the intake hub 44.

FIGS. 9A-9E show schematic views of a slidable tube fastening assembly comprising a slidable flange and a slidable tube faster. FIG. 9A shows a circular disk 59 having a central hole encircled by a connecting circular ridge 60 having an encircling neck portion 61. The connecting circular ridge 60 and the encircling neck portion 61 face distally a slidable tube fastener of FIG. 9B. FIG. 9B shows the slidable tube fastener comprising a clamp tube 62 having clamp levers 63 and 65, and a connecting circular rim clamp 67 in an unclamped configuration. The clamp tube 62 is configured to be concentrically squeezable by the clamp levers 63 and 65. The clamp lever 63 has an anchoring notch 64 which is configured to get reversibly anchored to an anchoring ridge 66 disposed on an outer surface of the clamp tube 62. The connecting circular rim clamp 67 comprises two opposing open circular ends 70 and 71, and a connecting circular slot 69. As shown in FIG. 9C, an inner opening 68 of the connecting circular rim clamp 67 is configured to mate with the encircling neck portion 61 of the slidable flange of FIG. 9A. The connecting circular slot 69 of the connecting circular rim clamp 67 is configured to couple with the connecting circular ridge 60 of the slidable flange of FIG. 9A. FIG. 9D shows the slidable tube fastener in a clamped configuration. FIG. 9E shows a schematic profile view of the slidable flange comprising a first planar surface 72 of the circular disk having the connecting circular ridge 60 facing the slidable tube fastener of FIG. 9A, and a second planar surface 73. The second planar surface 73 is configured with an adhesive for adhering to a skin of the chest wall. The adhesive is provided in a leakproof configuration comprising a protruding circular adhesive rim 74 encircling the central hole of the slidable flange to seal off a penetrated area of the chest wall by the introducer. In case a slit is made by a scalpel on the chest wall to introduce an introducer in a round tubular configuration, two opposite ends of the slit would remain open for a length upon introduction of the introducer as a source of air leak. The protruding circular adhesive rim 74 is provided in an O-ring configuration which is to be pushed against the two opposite ends of the slit wound so as to seal off these two opposite ends of the slit.

Figure 10A:
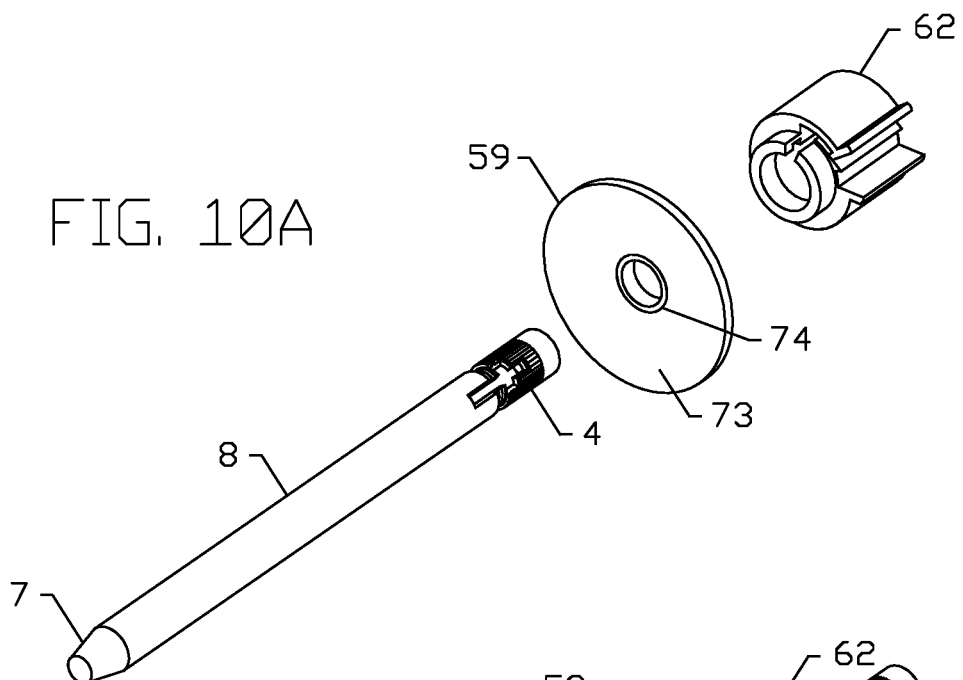
FIGS. 10A-10C show schematic views of placement of the slidable flange and the slidable tube fastener over the outer tube assembly.
Figure 10B:
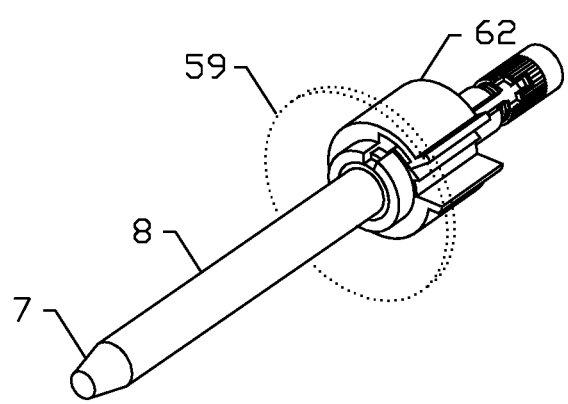
Figure 10C:
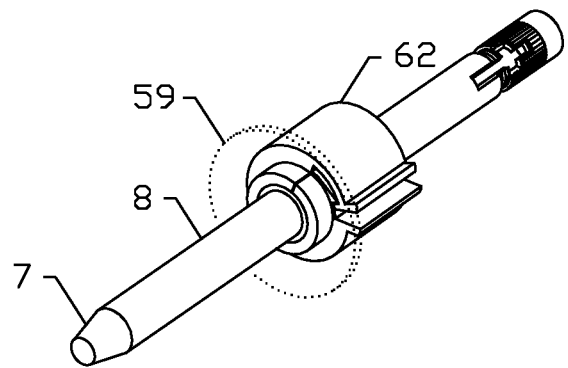

FIGS. 10A-10C show schematic views of placement of the slidable flange and the slidable tube fastener over the outer tube assembly. FIG. 10A shows individual components comprising the slidable flange 59 having the second planar surface 73 and the protruding circular adhesive rim 74, the clamp tube 62 of the slidable tube fastener, and the outer tube assembly having the proximal portion 7, the rotatable reversible air lock assembly 4 and the mid tubular shaft 8. As shown in FIG. 10B, the slidable flange and the slidable tube fastener in the unclamped configuration are disposed slidably over the mid tubular shaft 8 of the outer tube assembly. FIG. 10C shows the slidable flange and the slidable tube fastener in the clamped configuration disposed slidably over the mid tubular shaft 8 of the outer tube assembly in order to reversibly fasten the outer tube assembly.

FIGS. 11A-11C show schematic views of an angled slidable flange and an angled slidable tube fastener, and their placement over the outer tube assembly. FIG. 11A shows a clamp tube 78 of the angled slidable tube fastener and an angled connecting circular rim clamp 79. The angled connecting circular rim clamp 79 is configured with first longitudinal side 80 of a tubular wall of the angled connecting circular rim clamp 79 being longer than second and opposite longitudinal side 81 of the tubular wall. A connecting circular slot 83 of the angled connecting circular rim clamp 79 is accordingly angled to a longitudinal axis of the clamp tube 78 and is in parallel with an angled inner opening 82. As shown in FIG. 11B, the angled slidable flange 75 comprises an angled connecting circular ridge 76 having an angled encircling neck portion 77. The angled connecting circular ridge 76 and the angled encircling neck portion 77 face distally the slidable tube fastener of FIG. 11A. As shown in FIG. 11C, the angled inner opening 82 of the angled connecting circular rim clamp 79 is configured to mate with the angled encircling neck portion 77 of the slidable flange of FIG. 11B. The angled connecting circular slot 83 of the angled connecting circular rim clamp 79 is configured to couple with the angled connecting circular ridge 76 of the angled slidable flange of FIG. 11B. The angled slidable flange 75 and the angled clamp tube 78 of the angled slidable tube fastener are configured to be angled to a longitudinal axis of the mid tubular shaft 8 of the outer tube assembly, which allows the outer tube assembly to be fastened at an angle to the chest wall.

Figure 12:
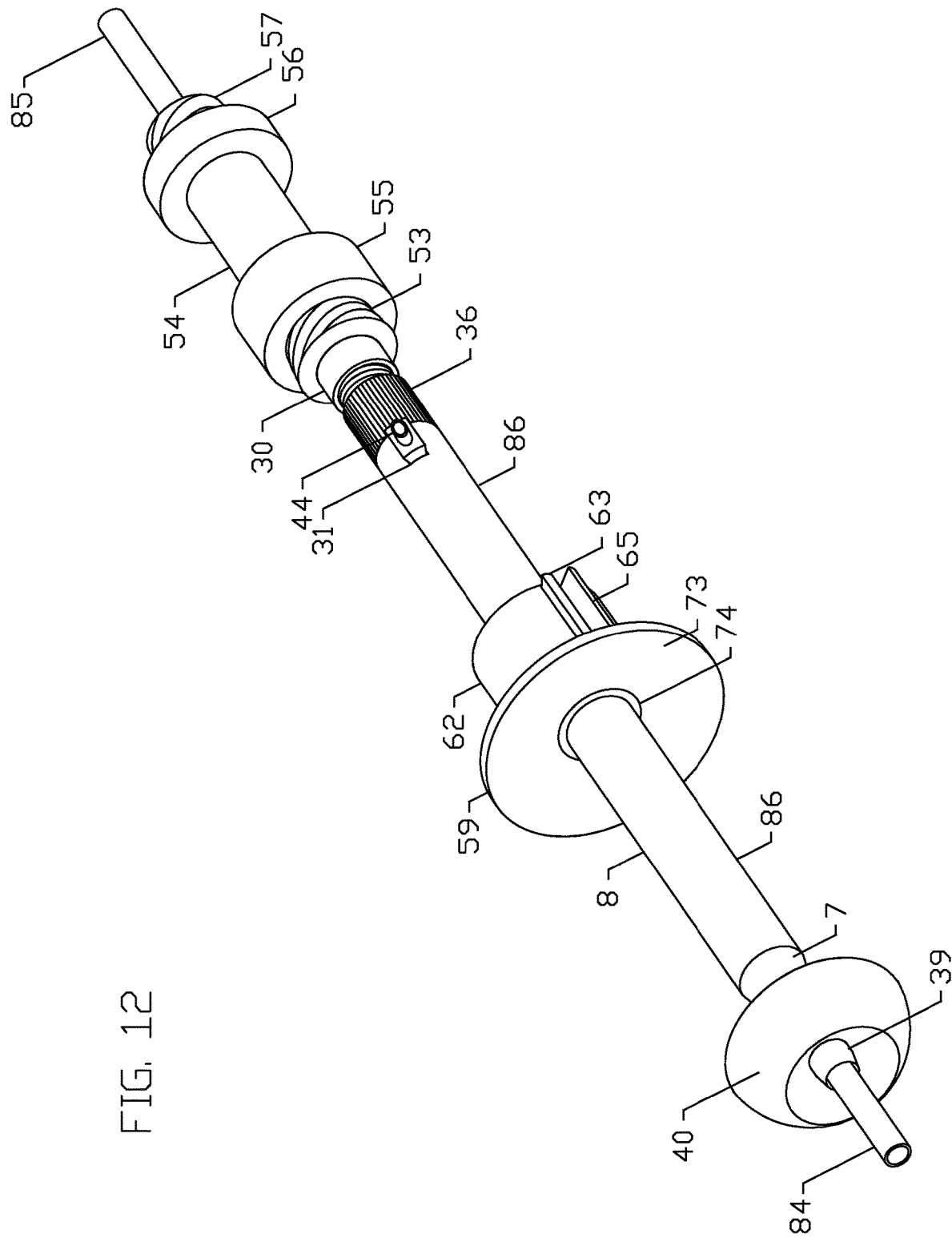
FIG. 12 shows a schematic view of the introducer in a fully deployed configuration, having a chest tube axially placed inside the introducer.

FIG. 12 shows a schematic view of the introducer in a fully deployed configuration, having a chest tube axially placed inside the introducer. Following withdrawal of the stylet shown in FIG. 2D after insertion of the introducer 86 into a pleural cavity, a sequence of deployment of the introducer 86 and the chest tube having a proximal portion 84 and a distal portion 85 starts with the intake hub 44 with the neck portion 43 of the slidable inner tube assembly being advanced forward to, the proximal linear open slot 31 and followed by tightening of the rotatable screw-cap 36 about the rotatable reversible air lock assembly, thus providing a step (1) of leakproof locking of the rotatable reversible air lock assembly as shown in FIGS. 8A-8C. Synchronized with the forward advancement of the intake hub 44 with the neck portion 43 of the slidable inner tube assembly to the proximal linear open slot 31, the proximal portion 39 of the slidable inner tube assembly having the internal balloon 40 is advanced forward out of the proximal portion 7 of the outer tube assembly. At this step (2), the internal balloon 40 is pushed forward in the configuration as shown in FIGS. 6A-6C in order to maintain the leakproof seal around the proximal portion 7 of the outer tube assembly. Following the air-locking of the rotatable reversible air lock assembly, the internal balloon 40 is inflated and the trocar shown in FIG. 2C is removed. While the internal cylindrical bar of the distal tube fastener assembly prevents air leakage through the central longitudinal slit 51 as illustrated in FIGS. 7A-7D, the proximal end 84 of the chest tube is threaded through the central longitudinal slit 51 of FIG. 7A out of the proximal portion 39 of the slidable inner tube assembly. Once the chest tube is properly located in the pleural cavity, the screw-caps 55 and 56 of the distal tube fastener assembly leakproofly tighten the proximal tubular portion 53 and the distal tubular portion 57 respectively (3). Subsequently, the slidable flange 59 and the slidable tube fastener having the clamp tube 62 and the clamp lever 63 and 65 are firmly pushed against the chest wall, which allows the second planar surface 73 to adhere to the chest wall. The protruding circular adhesive rim 74 provides leakproof adhesion between the second planar surface of the slidable flange and the chest wall (4). Once the slidable flange is tightly adhered to the chest wall, the slidable tube fastener is clamped to fasten the mid tubular shaft 8 of the outer tube assembly. The aforementioned four steps of air locking allow the introducer and the chest tube to be placed non-surgically without a need to suture an insertion site of the introducer for prevention of the air leak.

It is to be understood that the aforementioned description of the apparatus is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A non-surgical chest tube introducer, comprising:
    an outer tube assembly, a slidable inner tube assembly, a slidable tube fastener assembly, and a trocar having a stylet inside the trocar;
    the outer tube assembly, wherein the outer tube assembly is provided in a sequential air-locking configuration, wherein the outer tube assembly is provided in a tube-in-tube configuration to slidably enclose the slidable inner tube assembly inside the outer tube assembly, wherein the outer tube assembly comprises a conical proximal portion configured to be reversibly sealed by an internal balloon of the slidable inner tube assembly placed inside the conical proximal portion, a mid tubular shaft having a pair of linear sliding slots disposed on an inner surface of the mid tubular shaft, a rotatable reversible air lock assembly disposed distal to the mid tubular shaft and configured to couple with an intake hub assembly of the slidable inner tube assembly, and a distal tube fastener assembly configured to leakproofly fasten a tubular catheter movably placed inside the distal tube fastener assembly, wherein the mid tubular shaft of the outer tube assembly connects the conical proximal portion to the rotatable reversible air lock assembly, and wherein a proximal end of the distal tube fastener fixedly adjoins a distal end of the rotatable reversible air lock assembly;

the slidable inner tube assembly, wherein the slidable inner tube assembly is slidably enclosed inside the outer tube assembly, wherein the slidable inner tube assembly comprises the internal balloon fixedly disposed thereof on an outer surface of a proximal portion of the slidable inner tube assembly, a mid tubular shaft having a pair of linear sliding rails, a conduit connecting the internal balloon and the intake hub assembly, and the intake hub assembly disposed thereof at a distal portion of the slidable inner tube assembly, wherein the mid tubular shaft connects the proximal portion of the slidable inner tube assembly to the intake hub assembly, wherein the internal balloon is partially inflated in an unengaged configuration in order to sealably fill a space inside the conical proximal portion of the outer tube assembly, wherein the linear sliding rail is configured to slidably couple with the linear sliding slot of the outer tube assembly, wherein the conduit is configured to be placed inside the linear sliding rail, wherein the intake hub assembly is configured to slidably couple with the rotatable reversible air lock assembly of the outer tube assembly, and wherein the intake hub assembly is configured to move the slidable inner tube assembly back and forth inside the outer tube assembly; and the slidable tube fastener assembly, wherein the slidable tube fastener assembly comprises a slidable flange and a slidable tube fastener, wherein the slidable flange and the slidable tube fastener are slidably placed over the outer tube assembly, wherein the slidable flange is provided in a disk configuration having a central hole, wherein a first surface of the slidable flange is configured to reversibly couple with the slidable tube fastener, wherein a second surface of the slidable flange is configured to leakproofly adhere to a skin of an introduction site of a chest wall, wherein a transverse axis of the slidable flange is angled to a longitudinal axis of the outer tube assembly, wherein the slidable tube fastener is provided in a reversible clamp configuration to reversibly fasten the outer tube assembly, wherein the slidable tube fastener is configured to reversibly couple with the slidable flange, and wherein a transverse axis of the slidable tube fastener is angled to the longitudinal axis of the outer tube assembly and is in parallel with the transverse axis of the slidable flange.

2. The non-surgical chest tube introducer according to claim 1, wherein the rotatable reversible air lock assembly of the outer tube assembly comprises:

a tubular portion, and a screw-cap;

the tubular portion, provided in a longitudinal tubular configuration, wherein the tubular portion is placed in the screw-cap of the rotatable reversible air lock assembly, wherein an outer surface of a tubular wall of the tubular portion is provided with helical threads disposed thereof on the outer surface of the tubular wall of the tubular portion, wherein the helical threads of the tubular portion is configured to mate with an internal helical thread of the screw-cap of the rotatable reversible air lock assembly, wherein the tubular portion is provided with a linear open slot disposed longitudinally thereof in the tubular wall of the tubular portion, wherein the linear open slot is configured to slidably couple with the intake hub assembly of the slidable inner tube assembly, wherein a part of the linear open slot is configured to be open and to be closed by helically rotating the screw-cap of the rotatable reversible air lock assembly about the tubular portion, and wherein the tubular portion is configured to leakproofly lock the intake hub assembly by closing the part of the linear open slot by the screw-cap of the rotatable reversible air lock assembly.

3. The non-surgical chest tube introducer according to claim 1, wherein the distal tube fastener assembly of the outer tube assembly comprises:

a tubular portion, a pair of screw-caps, and a cylindrical bar;

the tubular portion, having a proximal tubular portion, a mid tubular portion, and a distal tubular portion, wherein the proximal tubular portion is provided in a tapered configuration with a larger tubular size of a proximal end of the proximal tubular portion than that of a distal end of the proximal tubular portion, wherein the distal tubular portion is provided in a tapered configuration with a larger tubular size of a distal end of the distal tubular portion than that of a proximal end of the distal tubular portion, wherein the proximal tubular portion is configured to fasten a proximal portion of the cylindrical bar inside the proximal tubular portion by a first screw-cap slidably placed over the proximal tubular portion, wherein the distal tubular portion is configured to fasten a distal portion of the cylindrical bar inside the distal tubular portion by a second screw-cap slidably placed over the distal tubular portion, and wherein the tubular portion is configured to slidably house the cylindrical bar inside the tubular portion; and the cylindrical bar, provided as an elastomeric longitudinal bar, wherein the cylindrical bar is configured to be slidably and movably placed in the tubular portion, wherein the cylindrical bar is provided with a central slit axially disposed along a longitudinal axis of the cylindrical bar, wherein the central slit is configured to be closed in an unengaged configuration, wherein the central slit in the unengaged configuration prevents air leakage across the central slit, wherein the central slit is configured to let the tubular catheter pass therethrough the central slit, and wherein the cylindrical bar is configured to be reversibly fastened by the tubular portion of the distal tube fastener assembly.

4. The non-surgical chest tube introducer according to claim 1, wherein the internal balloon of the slidable inner tube assembly further comprises:

wherein the internal balloon inside the conical proximal portion of the outer tube assembly is configured to be partially inflated to fill the space between the internal balloon and the conical proximal portion in the unengaged configuration so as to reversibly seal the space between the internal balloon and the conical proximal portion, and wherein the reversible sealing between the internal balloon and the conical proximal portion is maintained during forward advancement of the internal balloon through the conical proximal portion by the partially inflated internal balloon; and wherein the partially inflated internal balloon is configured to be fully inflated following the forward advancement of the partially inflated internal balloon through the conical proximal portion by insufflating a gas through an intake hub of the intake hub assembly.

5. The non-surgical chest tube introducer according to claim 1, wherein the intake hub assembly of the slidable inner tube assembly comprises:

the intake hub, and an elastomeric ring;

the intake hub, wherein the intake hub is connected at an angle to the distal portion of the slidable inner tube assembly, wherein the connection between the intake hub and the distal portion of the slidable inner tube assembly is reinforced by an intake hub neck portion provided in a rectangular configuration, wherein forward advancement of the intake hub neck portion inside the linear open slot of the tubular portion of the rotatable reversible air lock assembly is configured to synchronize with the forward advancement of the internal balloon of the slidable inner tube assembly out of the conical proximal portion of the outer tube assembly, wherein the intake hub neck portion is configured to sealably and slidably couple with the linear open slot, and wherein the intake hub neck portion is configured to be leakproofly lockable by closing the part of the linear open slot by the screw-cap of the rotatable reversible air lock assembly following the forward advancement of the internal balloon through the conical proximal portion of the outer tube assembly; and the elastomeric ring, wherein the elastomeric ring is disposed thereof inside the tubular portion of the rotatable reversible air lock assembly of the outer tube assembly, wherein the elastomeric ring is configured to fixedly encircle a part of the distal portion of the slidable inner tube assembly, wherein the elastomeric ring is configured to leakproofly seal a space between the tubular portion of the rotatable reversible air lock assembly and the elastomeric ring, and wherein the elastomeric ring is configured to be slidably movable inside the tubular portion of the rotatable reversible air lock assembly.

6. The non-surgical chest tube introducer according to claim 1, wherein the sequential air-locking configuration of the outer tube assembly upon introduction of the non-surgical chest tube introducer into a pleural cavity comprises:

(1) the rotatable reversible air lock assembly of the outer tube assembly reversibly leakproofly-locking the intake hub neck portion of the intake hub assembly of the slidable inner tube assembly, wherein the tubular portion of the rotatable reversible air lock assembly leakproofly locks the intake hub neck portion of the intake hub assembly by closing the part of the linear open slot by the screw-cap of the rotatable reversible air lock assembly, wherein the intake hub neck portion of the intake hub assembly is slidably placed in the linear open slot of the rotatable reversible air lock assembly;

(2) the internal balloon of the slidable inner tube assembly reversibly sealing the conical proximal portion of the outer tube assembly, wherein the internal balloon is placed in the conical proximal portion in the unengaged configuration, wherein the internal balloon inside the conical proximal portion is partially inflated to fill the space between the internal balloon and the conical proximal portion in the unengaged configuration, and wherein the reversible sealing of the conical proximal portion is maintained during the forward advancement of the proximal portion of the slidable inner tube assembly through the conical proximal portion by the partially inflated internal balloon; and (3) the distal tube fastener of the outer tube assembly reversibly fastening the tubular catheter inside the distal tube fastener, wherein the proximal tubular portion of the distal tube fastener is configured to fasten the proximal portion of the cylindrical bar of the distal tube fastener inside the proximal tubular portion by the first screw-cap slidably placed over the proximal tubular portion, and wherein the distal tubular portion of the distal tube fastener is configured to fasten the distal portion of the cylindrical bar inside the distal tubular portion by the second screw-cap slidably placed over the distal tubular portion.

7. The non-surgical chest tube introducer according to claim 1, wherein the second surface of the slidable tube fastener assembly further comprises:

a protruding circular adhesive rim encircling the central hole, wherein the protruding circular adhesive rim is disposed on the second surface of the slidable flange, wherein the second surface of the slidable flange faces the skin of the chest wall, and wherein the protruding circular adhesive rim is provided in a configuration to seal off the introduction site of the chest wall through which the non-surgical chest tube introducer is introduced into the pleural cavity.

* * * * *